United States Patent [19]

Rhodes et al.

[11] 4,137,751
[45] Feb. 6, 1979

[54] AERIAL PROSPECTING

[75] Inventors: John R. Rhodes; Robert D. Sieberg; Morris C. Taylor; John C. Westkaemper, all of Austin, Tex.; Robert C. Young, Idaho Falls, Id.

[73] Assignee: Columbia Scientific Industries, Inc., Austin, Tex.

[21] Appl. No.: 554,114

[22] Filed: Feb. 28, 1975

Related U.S. Application Data

[63] Continuation of Ser. No. 301,283, Oct. 27, 1972, abandoned.

[51] Int. Cl.² ................. B01D 46/00; G01N 31/06
[52] U.S. Cl. ................................................. 73/28
[58] Field of Search ............... 73/28, 170 R, 421.5 R, 73/194 R, 214; 55/270, 428, 459, 461; 23/230 EP

[56] References Cited

U.S. PATENT DOCUMENTS

| | | | |
|---|---|---|---|
| 2,943,698 | 7/1960 | Bishop | 55/459 R |
| 3,252,323 | 5/1966 | Torgeson | 73/170 R |
| 3,309,518 | 3/1967 | Weiss | 73/28 |
| 3,334,516 | 8/1967 | Cedrone | 55/270 |
| 3,554,005 | 1/1971 | Koblin et al. | 73/28 |
| 3,605,485 | 9/1971 | Badzioch et al. | 73/28 |
| 3,654,801 | 4/1972 | Keefer et al. | 73/28 |
| 3,759,617 | 9/1973 | Barringer | 73/28 |
| 3,768,302 | 10/1973 | Barringer | 73/28 |

Primary Examiner—Stephen A. Kreitman
Attorney, Agent, or Firm—Arnold, White & Durkee

[57] ABSTRACT

A method and apparatus are disclosed for improved collection of airborne particles in an airborne prospecting method. A high volume of air is sampled and processed through a cyclone separator to achieve a high concentration of particle collection on a collecting surface. The collected particles may be analyzed as to mineral element type and correlated with the geographical position of collection to permit a deduction as to the type of minerals and soil in the terrain below.

9 Claims, 5 Drawing Figures

AERIAL PROSPECTING

This is a continuation of application Ser. No. 301,283, filed 10/27/72, now abandoned.

FIELD OF THE INVENTION

This invention relates broadly to geophysical exploration and more particularly to aerial prospecting for mineral deposits.

In U.S. Pat. No. 3,309,518 to Oscar Weiss there is described a method for prospecting for minerals by collection of airborne dust particles (known as aerosols) and subsequent analysis in correlation with the position of collection of the particles. An aircraft is flown over the terrain where soil, rock and minerals of value are anticipated and dust particles are accumulated on separate collector surfaces that are exposed to a stream of dust-laden air. Subsequent chemical processing of the collector surfaces permits concentration of the dust particles in sufficient number and weight to permit an analysis of the chemical type of element represented by the dust particles. This analysis enables a determination to be made of the identity of the elements contained in mineralized rocks and soil. The procedure is based upon the assumption that the elemental composition of airborne dust at altitudes of up to a few hundred feet above the ground is correlated with that of the local soil and rocks.

The method of concentration of the dust particles described in the above-mentioned Pat. No. 3,309,518, is accomplished by dissolving the membrane filters on which the particles are collected to leave a solution with undissolved mineral particles suspended therein. The particles may then be concentrated by centrifuging and/or by filtrations.

It has been found, however, that the subsequent analysis and identification of the particles in such suspension of mineral particles is both tedious and costly. For example, there is invariably some loss of particles in the course of their concentration by the dissolving of the filters. In addition, the particulate sample becomes contaminated with foreign substances such as the flake-off from crucibles and containers. Some attempts have been made to improve the method of collection and concentration of airborne particles as evidenced by U.S. Pat. No. 3,462,995 to Oscar Weiss. In that patent is described a method of collecting airborne dust particles upon threads of a synthetic polymer material such as nylon and subsequent concentration by drawing the threads across a pad or block of particle retentive material. But even this method is slow, costly and subject to inaccuracy due to contamination.

SUMMARY OF THE INVENTION

Accordingly, the present invention provides a method and apparatus that permit collection and concentration of airborne particles in a quick and easy manner. The present invention employs the principle of centrifugal force to separate a large quantity of particles from the air.

In a preferred embodiment, a cyclone separator is employed to gather a high volume of dust-laden air in an airborne survey operation and deposit the dust particles on a suitable surface such as filter paper. The size of the cyclone separator and the inlet duct for the duct-laden airstream can be designed in such a way that a large volume of air can be processed to obtain enough data points per unit distance flown to resolve geochemical anomalies of a desired extent. The present invention avoids any necessity of further concentration of dust particles subsequent to the collecting steps. No solvents need be used to dissolve a collecting membrane nor do any collector threads need to be drawn across particle retentive pads.

By use of the cyclone separator in airborne prospecting according to the invention, it is possible to collect only the larger dust particles, say having diameters greater than 5 microns. This permits collection of particles that are more representative of the ground below than would be smaller particles.

BRIEF DESCRIPTION OF THE DRAWINGS

The invention is illustrated by way of example in the accompanying drawings which are briefly described as follows.

DESCRIPTION OF SPECIFIC EMBODIMENTS

Figure 1:
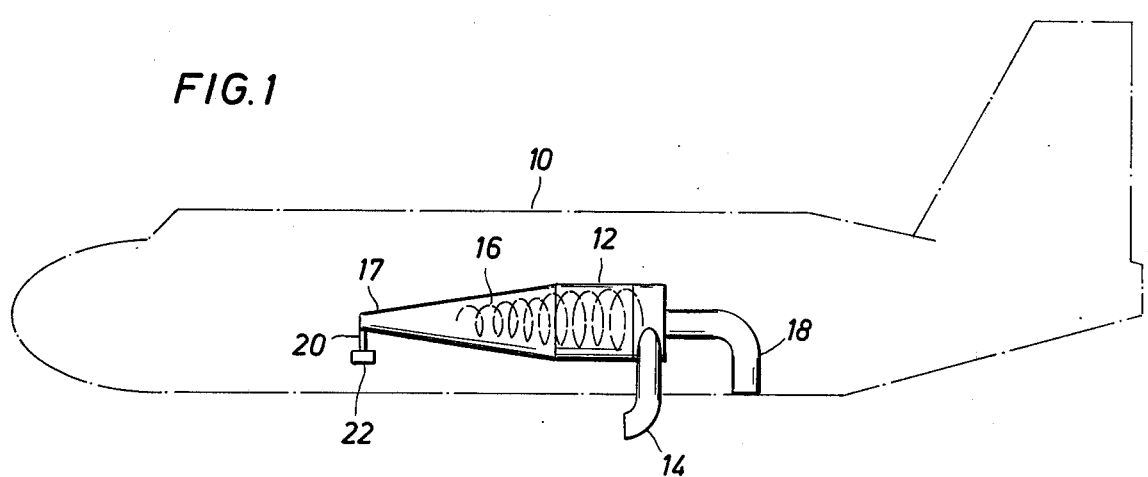
FIG. 1 is a diagramatic example of one form of airborne particle collection according to the invention.

It will be appreciated that the present invention can take many forms and embodiments, all of which would be impossible to describe or illustrate here. A limited number of forms of the invention and equipment embodying the invention will be described and illustrated for the purpose of giving an understanding of the invention. The true essence and spirit of the invention is defined in the appended claims, and it is not intended that the limited embodiments described in this specification and shown in the drawings should limit the invention.

Referring in detail to the drawings, and specifically to FIG. 1, an aircraft is shown by the dashed line 10 and a cyclone separator 12 is shown housed and mounted inside of its cabin. An air inlet duct 14 extends through the bottom wall of the cabin and is arranged to scoop a stream of air beneath the aircraft and direct it into cyclone separator 12. The cyclone separator 12 may be of conventional type such as obtainable from the Torit Corporation, Air Pollution Control Division, St. Paul, Minn.

Dust-laden air which is diverted into the cyclone 12 by the inlet duct 14 is driven in a spiraling configuration as shown by arrow 16 and all of the heavy particles are driven by centrifugal force toward the side wall of the cyclone separator. The inside walls of the cyclone separator 12 are shaped generally as a cone to force the swirling air into a cyclone configuration so that the heavy particles laden in the air are forcibly driven toward the apex 17 while the clean air is passed along the longitudinal axis and out through an exhaust duct 18 to the ambient air outside the aircraft.

The particles driven toward the apex 17 of the cyclone separator 12 are passed through a collector tube 20 and forcibly deposited upon a collector surface contained in a sample container 22.

Figure 2:
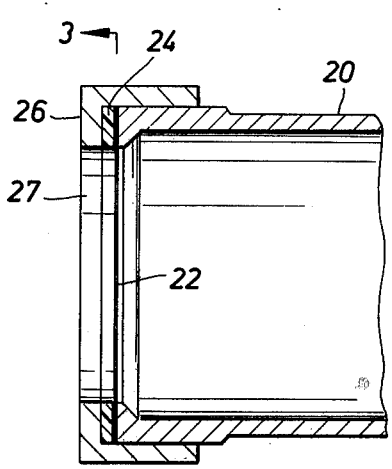
FIG. 2 is a sectional view of the particle sample collector according to one form of the invention.
Figure 3:
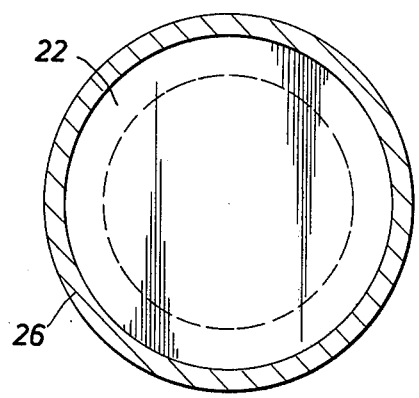
FIG. 3 is a sectional view taken along line 3—3 in FIG. 2.

In FIGS. 2 and 3 are shown an enlarged representation of the sample collector described in reference to FIG. 1. The sample collector comprises essentially a circular adhesive surface 22 where particles are deposited and is retained in place over the end of the collector tube 20 by means of a gasket ring 24 and an end cap 26. An aperture 27 in the end cap 26 provides equal pressure on both sides of the collector surface 22.

The collector surface 22 may be changed at desired intervals after there has been sufficient accumulation of dust particles dependent upon the flying speed of the aircraft and the volume of air being processed through the cyclone separator 12.

It has been found that for x-ray methods of analysis for identification of the elemental composition, dust particles are preferably spread evenly over a diameter of about 2 centimeters on a low background surface such as filter paper. Experimental tests have shown that the collectible dust concentrations over arid regions is of the order of 20 micrograms per cubic meter. Thus to collect one sample per mile at a flying speed of 2 miles per minute, the flow rate of processed air must be about 25,000 cubic feet per minute. When these criteria are met, concentration of the required number of particles may be achieved at the time of collection rather than in further processing steps.

Figure 4:
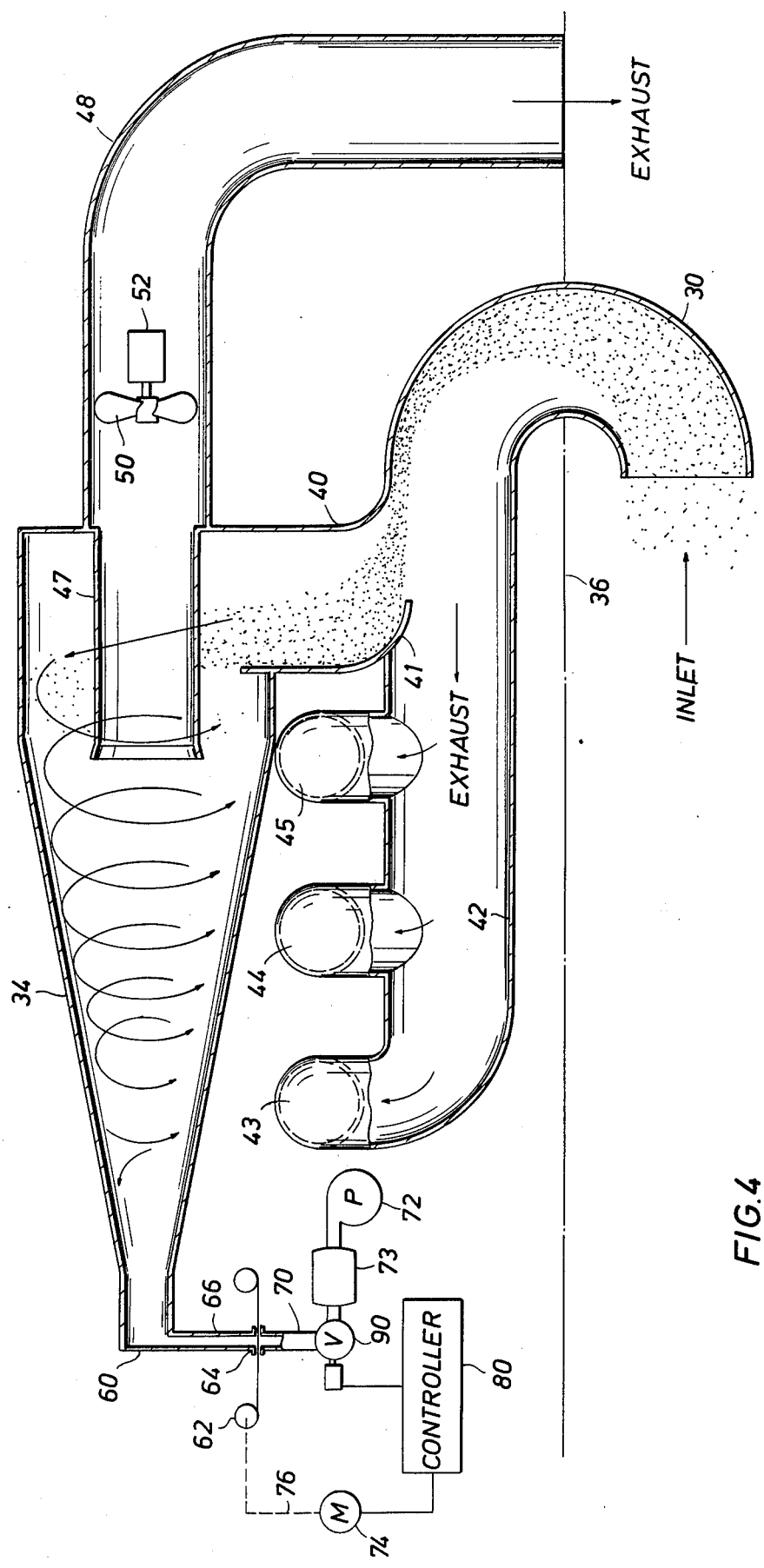
FIG. 4 is a schematic diagram of a particle collector according to another form of the invention employing a "shave-off" duct and automated movement of a collector tape.

FIG. 4 illustrates a schematic diagram of an apparatus which is designed to meet the above criteria. The collection method is based upon a centrifugal separation in two stages: First, through a "shave-off" duct 30 and; second, through a cyclone separator 34. The "shave-off" duct 30 is designed to provide a pre-concentration stage for particles delivered to the cyclone separator 34, and also allows a higher air flow rate to be processed. The "shave-off" duct 30 is shown in the form of a U-shaped tube, one end of which extends below the cabin of the aircraft base 36 to scoop a quantity of dust-laden air. The dust particles are shown in enlarged size as small dots to illustrate the principle that the particles are driven by centrifugal force against the outer radius of the shave-off duct 30 and are passed into the inlet duct 40 of the cyclone separator. A scoop 41 extends from the cyclone inlet duct 40 into the mid section between exhaust chamber 42 and shave-off duct 30 to aid in diverting the dust particles into the cyclone separator 34. The bulk of the air which passes into the shave-off duct 30 is passed into an exhaust chamber 42 which has a number of exhaust ports 43-45 vented to the air outside the aircraft. In one design, approximately 80% of the volume of the airstream passing into the shave-off duct 30 is passed through the exhaust chamber 42 and outward to the ambient air outside the aircraft through the exhaust port 43-45. The other 20% of the volume containing the bulk of the dust particles is passed up through the separator inlet duct 40. Different percentages of air volume can be diverted by adjusting the depth and inclination of scoop 41.

The design of the "shave-off" duct 30 is based upon the duct curvature, the air velocity and viscosity and the particle mass. A further description of the design characteristics necessary for a "shave-off" duct is given in "Industrial Gas Cleaning," by W. Strauss, Pergamon Press, 1966, Chapter 6.

The clean air exhaust for the cyclone separator 34 is passed from a tube 47 through an outlet duct 48 which terminates outside the cabin of the aircraft and is exposed to the ambient atmosphere. The stream of clean air passes along the axis of separator 34 and out through the tube 47 to exhaust. An exhaust fan 50 is mounted in the outlet duct 48 and is driven by a variable speed motor 52. The speed of the motor 52 is varied in order to provide a fan speed that will yield appropriate impedance matching arising because of the diversion of the airstream through the exhaust chamber 42.

Figure 5:
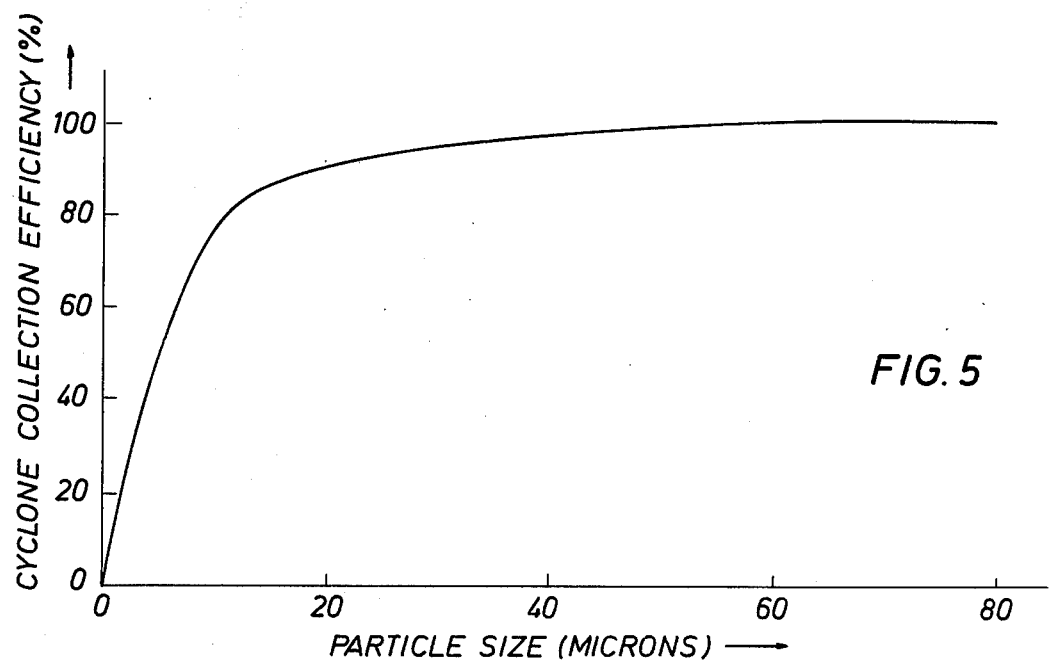
FIG. 5 is a chart of the efficiency of cyclone collection as a function of particle size.

Characteristics of cyclone separators are particularly adapted to airborne particle collection in airborne prospecting because centrifugal separation can process the large airflow rate required and is nearly 100% efficient for separating particles greater than about 10 microns diameter, while having a low collection efficiency for the unwanted sub-micron particles. A graph of the collection efficiency of a cyclone separator is shown in FIG. 5 of the drawing. It has been found that particles with diameters smaller than about 5 microns are not necessarily correlated closely with the elemental composition of centers of mineralization in rocks and soil on the terrain below. Thus the cyclone separator is ideally suited to eliminate the unwanted particles of this size but yet collect almost 100% of the larger particles that have a greater correlation with the minerals on the terrain below.

In order to provide an efficient and low cost means of collection and subsequent analysis of collected particles an automated mechanism is provided at the apex 60 of the cyclone separator. A roll of collector tape 62 is held by a transport mechanism (not shown) and passed in front of a collector station 64. Particles that are passed through the cyclone separator and deposited near the end of the apex 60 are driven through the collector tube 66 and deposited upon the surface of the collector tape 62 at the collector station 40. Collector tape 62 may be of various types but is now preferred to be filter tape. There is preferably a mask located at the collector station 64 with an aperture of 2 centimeters diameter so that all airborne particles are deposited on the collector tape 62 in an area of that size.

In order to draw the dust particles onto the collector tape 62 and imbed them, a partial vacuum of about 29 inches of mercury is provided on the collector tape 62 on the side opposite from the cyclone separator 34. Vacuum is provided by means of a vacuum line 70 that is connected from the collector station through a solenoid valve 90 to a vacuum tank 73. A vacuum pump 72 supplies vacuum pressure to vacuum tank 73 at required intervals.

The collector tape 62 is moved intermittently past the collector station 64 by means of a stepper motor 74 that is connected by a linkage 76 to a takeup reel containing the collector tape 62. The operation of the stepper motor 74 is controlled by a controller 80 which also controls the operation of the solenoid valve 90 connected in the vacuum line 70 between the collector's station 64 and the vacuum tank 73. The controller 80 is designed such that the solenoid valve 90 remains open to permit a vacuum upon the collector tape 62 during a collection period and is then released at the time the stepper motor 74 is energized to drive the tape to a new position. Experience has shown that the collector tape 62 should remain stationery for collection of a sample of particles for about 15 seconds before being moved to the next sample location. It is understood, however, that for different air speeds and desired particle concentrations and for different amounts of particles available in the air, that other periods of accumulation of dust particles will be required. Also the amount of time required to accumulate dust particles will vary with the method of analysis used. The dust samples are preferably deposited at approximately one inch intervals along the length of collector tape 62.

The rolls of collector tape 62 are subsequently analyzed in a laboratory for deposit mass per unit area and elemental mass per unit area using suitable methods such as x-ray transmission and x-ray fluoroscence respectively. The particle samples on the collector tape may be presented to the analyzer by the means of a tape transport mechanism similar to the one illustrated in FIG. 4. Further details of the analysis of the airborne particles will not be given here as this forms no part of the present invention.

What is claimed to have been invented or discovered is:

1. In the method of aerial prospecting involving the airborne collection of mineral particles, analysis of collected particles and correlation of the analysis data to the geographical position of airborne collection, the improved steps of collection comprising:
   divering an inlet stream of particle-laden air from the ambient atmosphere;
   dividing the inlet stream into two air streams, one containing the bulk of the particles laden in the inlet stream and the other containing the bulk of the air volume contained in the inlet stream;
   passing the air stream containing the bulk of particles into a cyclone separator and depositing the particles upon a collector surface.

2. Geochemical prospecting apparatus for use in conjunction with a flying aircraft having a cabin to collect and separate particles greater than about 5 microns in diameter from the particle-containing air outside said flying aircraft while at the same time permitting an accurate determination of the precise ground location over which such particle-containing air was collected, said apparatus comprising in combination:
   an inlet duct mounted in the aircraft and extending through a wall of the cabin for diverting a large volume of ambient particle-containing air from outside the aircraft into the interior of the cabin;
   a first centrifugal separation stage located at the air intake portion of said inlet duct wherein a major portion of the volume of air entering said inlet duct is removed from the collection process and the bulk of the particles contained in said major portion is concentrated in the remaining volume of air;
   a second centrifugal separation stage located inside the aircraft cabin downstream from said first centrifugal separation stage and coupled to the inlt duct whereby air-borne particles greater than about 5 microns in diameter are separated from the remaining air flowing through said duct and presented to a collector station; and
   a particle collector box coupled to the collector station and containing a collector surface on which the particles from said second centrifugal separation stage are deposited;
   said first centrifugal separation stage including a "shave-off" duct having a curved surface such that air entering the inlet duct is subjected to centrifugal force which directs the bulk of the particles and a minor portion of the air to the second centrifugal separation stage and directs the major portion of the air to an exhaust duct for passage to the atmosphere outside the aircraft; and
   said second centrifugal separation stage consists of a cyclone separator having an outlet duct for transferring back to the outside of the cabin air from which the particles have been separated and a collector station to which all of the separated particles are directed.

3. Apparatus according to claim 2 further including an exhaust fan mounted in the outlet duct for the cyclone separator.

4. Apparatus according to claim 3 wherein said exhaust fan is provided with a variable speed control to match the difference in impedance caused by the diversion through the cyclone separator of some of the air gathered by the inlet duct.

5. Apparatus according to claim 2 wherein the cyclone separator and inlet duct are constructed and arranged to provide an air flow rate of at least 25,000 cubic feet per minute.

6. Geochemical prospecting apparatus for use in conjunction with a flying aircraft having a cabin to collect and separate particles greater than about 5 microns in diameter from the particle-containing air outside said flying aircraft while at the same time permitting an accurate determination of the precise ground location over which such particle-containing air was collected, said apparatus comprising in combination:
   an inlet duct mounted in the aircraft and extending through a wall of the cabin for diverting a large volume of ambient particle-containing air from outside the aircraft into the interior of the cabin;
   a first centrifugal separation stage located at the air intake portion of said inlet duct wherein a major portion of the volume of air entering said inlet duct is removed from the collection process and the bulk of the particles contained in said major portion is concentrated in the remaining volume of air;
   a second centrifugal separation stage located inside the aircraft cabin downstream from said first centrifugal separation stage and coupled to the inlet duct whereby air-borne particles greater than about 5 microns in diameter are separated from the remaining air flowing through said duct and presented to a collector station; and
   a particle collector transport for passing a roll of collector tape intermittently past the outflow from said second centrifugal separation stage at said collector station;
   said first centrifugal separation stage including a "shave-off" duct having a curved surface such that air entering the inlet duct is subjected to centrifugal force which directs the bulk of the particles and a minor portion of the air to the second centrifugal separation stage and directs the major portion of the air to an exhaust duct for passage to the atmosphere outside the aircraft; and
   said second centrifugal separation stage consists of a cyclone separator having an outlet duct for transferring back to the outside of the cabin air from which the particles have been separated and a collector station to which all of the separated particles are directed.

7. Apparatus according to claim 6 wherein a vacuum is provided at the collector station to draw the particles against the collector tape and imbed them therein.

8. Apparatus according to claim 7 wherein a controller is provided to operate the transport to drive the collector tape past the collector station at intermittent increments of time and to release the vacuum provided at the collector station during movement of the collector tape.

9. Geochemical prospecting apparatus for use in conjunction with a flying aircraft having a cabin to collect and separate particles greater than about 5 microns in diameter from the particle-containing air outside said flying aircraft while at the same time permitting an accurate determination of the precise ground location over which such particle-containing air was collected, said apparatus comprising in combination:

an inlet duct mounted in the aircraft and extending through a wall of the cabin for diverting a large volume of ambient particle-containing air from outside the aircraft into the interior of the cabin;

a first centrifugal separation stage located at the air intake portion of said inlet duct wherein a major portion of the volume of air entering said inlet duct is removed from the collection process and the bulk of the particles contained in said major portion is concentrated in the remaining volume of air;

a second centrifugal separation stage located inside the aircraft cabin downstream from said first centrifugal separation stage and coupled to the inlet duct whereby air-borne particles greater than about 5 microns in diameter are separated from the remaining air flowing through said duct and presented to a collector station; and a particle collector box coupled to the collector station and containing a collector surface on which the particles from said centrifugal separation stage are deposited;

said first centrifugal separation stage including a "shave-off" duct having a curved surface such that air entering the inlet duct is subjected to centrifugal force which directs the bulk of the particles and a minor portion of the air to the second centrifugal separation stage and directs the major portion of the air to an exhaust duct for passage to the atmosphere outside the aircraft; and said second centrifugal stage consists of a cyclone separator having an outlet duct for transferring back to the outside of the cabin air from which the particles have been separated, a collector station to which all of the separated particles are directed and a variable speed exhaust fan to match the difference in impedance caused by the diversion through the cyclone separator of some of the air gathered by the first centrifugal separation stage.

* * * * *